(12) United States Patent
Kubicek et al.

(10) Patent No.: US 10,112,203 B2
(45) Date of Patent: Oct. 30, 2018

(54) PORTABLE VOLATILE MATERIAL DISPENSER AND METHOD OF SIMULATING A FLAME IN SAME

(71) Applicant: S.C. Johnson & Son, Inc., Racine, WI (US)

(72) Inventors: Chris A. Kubicek, East Troy, WI (US); Scott D. Walter, Twin Lakes, WI (US); Alexander S. Park, Chicago, IL (US); Sajid Patel, Arlington Heights, IL (US); Steven V. Bisbikis, Hawthorn Woods, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 344 days.

(21) Appl. No.: 13/864,690

(22) Filed: Apr. 17, 2013

(65) Prior Publication Data

US 2014/0312136 A1 Oct. 23, 2014

(51) Int. Cl.
*B05B 7/02* (2006.01)
*B05B 17/06* (2006.01)
(Continued)

(52) U.S. Cl.
CPC ............... *B05B 7/02* (2013.01); *A61L 9/122* (2013.01); *A61L 9/14* (2013.01); *B05B 17/0615* (2013.01);
(Continued)

(58) Field of Classification Search
CPC ...... A61L 9/12; A61L 9/127; A61L 2209/111; A61L 2209/12; A61L 2209/132;
(Continued)

(56) References Cited

U.S. PATENT DOCUMENTS 3,970,250 A 7/1976 Drews
4,078,891 A 3/1978 Madjar
(Continued)

FOREIGN PATENT DOCUMENTS

CN 202813634 U 3/2013
EP 1878449 A1 1/2008
(Continued)

OTHER PUBLICATIONS

PCT/US2014/020137 International Search Report and Written Opinion dated Sep. 2, 2014.

*Primary Examiner* — Alexander Valvis
*Assistant Examiner* — Christopher R Dandridge
(74) *Attorney, Agent, or Firm* — Quarles & Brady LLP

(57) ABSTRACT

A portable volatile material dispenser includes a housing having a top wall and at least one side wall and an opening formed within the top wall of the housing. A volatile material actuator is disposed within the housing and a manifold is in fluid communication with and extends between the volatile material actuator and the opening to move volatile material in the form of a mist from the volatile material actuator, through the manifold, and out the opening. A container holding a fluid is disposed within the housing and in fluid communication with the volatile material actuator. An air flow generator disposed within the housing and positioned to create a flow of air out of the dispenser through the opening for moving the mist from the dispenser.

11 Claims, 8 Drawing Sheets

(51) Int. Cl.
*A61L 9/12* (2006.01)
*A61L 9/14* (2006.01)

(52) U.S. Cl.
CPC ...... *A61L 2209/111* (2013.01); *A61L 2209/12* (2013.01); *A61L 2209/132* (2013.01)

(58) Field of Classification Search
CPC ...... A61L 2209/122; A61L 9/14; A61L 9/122; B05B 7/2408; B05B 7/02; B05B 7/2424; B05B 7/2435; B05B 7/24; A47G 2019/2227
USPC .... 239/34, 53, 44, 302; 362/101, 97.1, 97.2, 362/642, 644, 646, 640, 253, 643, 96, 362/653
See application file for complete search history.

(56) References Cited

U.S. PATENT DOCUMENTS

| | | | |
|---|---|---|---|
| 4,850,534 A | 7/1989 | Takahashi et al. | |
| 5,312,281 A | 5/1994 | Takahashi et al. | |
| 5,642,580 A | 7/1997 | Hess et al. | |
| 5,662,835 A | 9/1997 | Collingwood | |
| 5,700,430 A | 12/1997 | Bonnema et al. | |
| 5,928,605 A | 7/1999 | Bonnema et al. | |
| 5,970,643 A | 10/1999 | Gawel, Jr. | |
| 5,989,128 A | 11/1999 | Baker et al. | |
| 6,154,607 A | 11/2000 | Flashinski et al. | |
| 6,273,342 B1 | 8/2001 | Terada et al. | |
| 6,385,881 B1 | 5/2002 | Hess | |
| 6,454,425 B1 | 9/2002 | Lin | |
| 6,783,081 B2 | 8/2004 | Pedrotti et al. | |
| 6,802,782 B2 | 10/2004 | Hall et al. | |
| 6,857,746 B2 | 2/2005 | Dyner | |
| 6,901,926 B2 | 6/2005 | Yamamoto et al. | |
| 6,944,982 B2 | 9/2005 | Schroeter et al. | |
| 6,953,401 B2 | 10/2005 | Starr | |
| 7,066,637 B2 | 6/2006 | Nozawa et al. | |
| 7,093,949 B2* | 8/2006 | Hart | A01M 1/2033 362/253 |
| 7,162,820 B2 | 1/2007 | Hess et al. | |
| 7,168,630 B1 | 1/2007 | Ketcha et al. | |
| 7,424,979 B1 | 9/2008 | Chen | |
| 7,484,860 B2* | 2/2009 | Demarest | A01M 1/2083 362/101 |
| 7,490,815 B2 | 2/2009 | Tollens et al. | |
| 7,499,632 B2 | 3/2009 | Granger et al. | |
| 7,651,230 B2 | 1/2010 | O'Neill | |
| 7,712,249 B1 | 5/2010 | Modlin et al. | |
| 7,762,897 B2 | 7/2010 | Starr et al. | |
| 7,832,655 B2 | 11/2010 | Tollens et al. | |
| 7,959,132 B2 | 6/2011 | Butler et al. | |
| 7,963,460 B2 | 6/2011 | Jorgensen | |
| 7,967,690 B2 | 6/2011 | O'Neill | |
| 7,992,801 B2 | 8/2011 | Jorgensen | |
| 8,029,153 B2* | 10/2011 | Jorgensen | A61L 9/14 362/101 |
| 8,043,569 B2 | 10/2011 | Tranzeat | |
| 8,136,276 B2 | 3/2012 | O'Neill | |
| 8,196,903 B2 | 6/2012 | Jorgensen | |
| 8,281,514 B2* | 10/2012 | Fleming | 43/129 |
| 8,296,993 B2 | 10/2012 | Modlin et al. | |
| 8,328,115 B2 | 12/2012 | Feriani et al. | |
| 8,359,785 B2 | 1/2013 | Ohtsuka et al. | |
| 8,371,740 B2* | 2/2013 | Pestl | F21V 33/004 362/101 |
| 8,413,358 B2 | 4/2013 | Betz et al. | |
| 8,783,888 B2* | 7/2014 | McCavit | A61L 9/122 362/162 |
| 8,881,945 B2* | 11/2014 | Gasper | A01M 1/2038 222/1 |
| 8,925,905 B2* | 1/2015 | Vieira | A01M 1/2033 261/101 |
| 9,013,961 B1* | 4/2015 | Nicholson et al. | 367/139 |
| 2001/0033488 A1 | 10/2001 | Chliwnyj et al. | |
| 2002/0080601 A1 | 6/2002 | Meltzer | |
| 2003/0081408 A1* | 5/2003 | Tai | 362/101 |
| 2004/0256487 A1* | 12/2004 | Collins et al. | 239/338 |
| 2004/0257798 A1 | 12/2004 | Hart et al. | |
| 2006/0043619 A1* | 3/2006 | Brown | A01M 1/2033 261/19 |
| 2006/0120080 A1* | 6/2006 | Sipinski | A01M 1/205 362/253 |
| 2007/0122306 A1 | 5/2007 | Brown et al. | |
| 2008/0036332 A1 | 2/2008 | Helf | |
| 2008/0093474 A1* | 4/2008 | Suissa et al. | 239/34 |
| 2008/0112154 A1* | 5/2008 | Reichow | F21S 10/04 362/96 |
| 2008/0150453 A1 | 6/2008 | Medley et al. | |
| 2008/0216366 A1 | 9/2008 | Purton et al. | |
| 2008/0223953 A1 | 9/2008 | Tomono et al. | |
| 2009/0080871 A1 | 3/2009 | Chiu | |
| 2010/0299980 A1 | 12/2010 | Betz et al. | |
| 2011/0114750 A1 | 5/2011 | Duru | |
| 2011/0250978 A1 | 10/2011 | O'Neill | |
| 2012/0300433 A1 | 11/2012 | Lee | |
| 2013/0068788 A1* | 3/2013 | Gasper | A01M 1/2038 222/63 |
| 2013/0126633 A1 | 5/2013 | Powell et al. | |
| 2013/0223043 A1* | 8/2013 | Ray | F21V 33/00 362/96 |
| 2013/0291859 A1* | 11/2013 | Casey et al. | 128/200.14 |
| 2014/0049941 A1* | 2/2014 | Lee | A61L 9/122 362/96 |

FOREIGN PATENT DOCUMENTS

| | | |
|---|---|---|
| JP | 1991-314317 | 6/1993 |
| JP | 2004-038498 | 8/2005 |
| JP | 2009-003903 U | 9/2009 |
| JP | 2009-006073 U | 10/2009 |
| JP | 2009-006858 U | 11/2009 |
| WO | WO2005003623 A2 | 1/2005 |
| WO | WO2007056147 A1 | 5/2007 |
| WO | WO2008016867 A2 | 2/2008 |
| WO | WO 2012/066068 | 5/2012 |

* cited by examiner

PORTABLE VOLATILE MATERIAL DISPENSER AND METHOD OF SIMULATING A FLAME IN SAME

BACKGROUND OF THE INVENTION

1. Field of the Invention

The present invention relates generally to volatile material dispensers and, more particularly, to volatile material dispensers that emit a mist of volatile material therefrom.

2. Description of the Background of the Invention

Various volatile material dispensers are known in the prior art and generally include a housing with a refill inserted therein. The refill generally includes a container for holding a volatile material therein. In some dispensers, the volatile material is passively emitted therefrom. In other dispensers, a diffusion element is utilized to facilitate the dispensing of the volatile material. Examples of diffusion elements include heaters, piezoelectric elements, venturis, fans, aerosol actuators, and the like. Regardless of the manner in which the volatile material is emitted, once the volatile material has been expended from the refill, the refill is removed by a user and replaced with a new refill.

Many consumers desire a multi-sensory experience when purchasing and using a volatile material dispenser. For example, consumers would like to see lights and/or hear music in combination with the scent experience from a volatile material dispenser. Dispensers have therefore been designed to combine scent, light, and/or sound to enhance the user sensory experience. For example, one such dispenser includes a housing capable of accepting a volatile material refill, wherein volatile material is emitting from the refill by way of a piezoelectric actuator. The dispenser further includes a light emitting diode (LED) that flickers to emulate the light of a candle. The smell of the volatile material in combination with the LED provide the consumer with the experience of a real scented candle.

SUMMARY

According to one illustrative embodiment, a portable volatile material dispenser includes a housing having a top wall and at least one side wall and an opening formed within the top wall of the housing. A volatile material actuator is disposed within the housing and a manifold is in fluid communication with and extends between the volatile material actuator and the opening to move volatile material in the form of a mist from the volatile material actuator, through the manifold, and out the opening. A container holding a fluid is disposed within the housing and in fluid communication with the volatile material actuator. An air flow generator is disposed within the housing and positioned to create a flow of air out of the dispenser through the opening for moving the mist from the dispenser.

According to another illustrative embodiment, a portable volatile material dispenser comprises a housing, an opening formed within a wall of the housing, and a volatile material actuator spaced from the opening for dispensing mist through the opening. A container holding a fluid is disposed within the housing in communication with the volatile material actuator to transport the fluid to the volatile material actuator. An air flow generator is positioned within the housing to create a flow of air out of the dispenser through the opening for moving the volatile material in the form of a mist from the dispenser. A plurality of light emitting diodes are disposed longitudinally below and aligned with a profile of the opening for illuminating the mist emitted from the dispenser to simulate a flame.

According to a further illustrative embodiment, a method of simulating a flame in a portable volatile material dispenser includes the step of dispensing mist from a volatile material actuator within the portable dispenser, wherein the mist is dispensed through an opening in the portable dispenser. The method further includes the steps of providing a flow of air through the opening to move the mist out of the dispenser and illuminating portions of the mist to create the illusion of a flame.

BRIEF DESCRIPTION OF THE DRAWINGS

Other aspects and advantages of the present invention will become apparent upon consideration of the following detailed description, wherein similar structures have like or similar reference numerals.

DETAILED DESCRIPTION

The present invention is directed to volatile material dispensers and methods of emitting volatile materials therefrom. While the present invention may be embodied in many different forms, several specific embodiments are discussed herein with the understanding that the present invention is to be considered only as an exemplification of the principles of the invention, and it is not intended to limit the invention to the embodiments illustrated.

Figure 1:
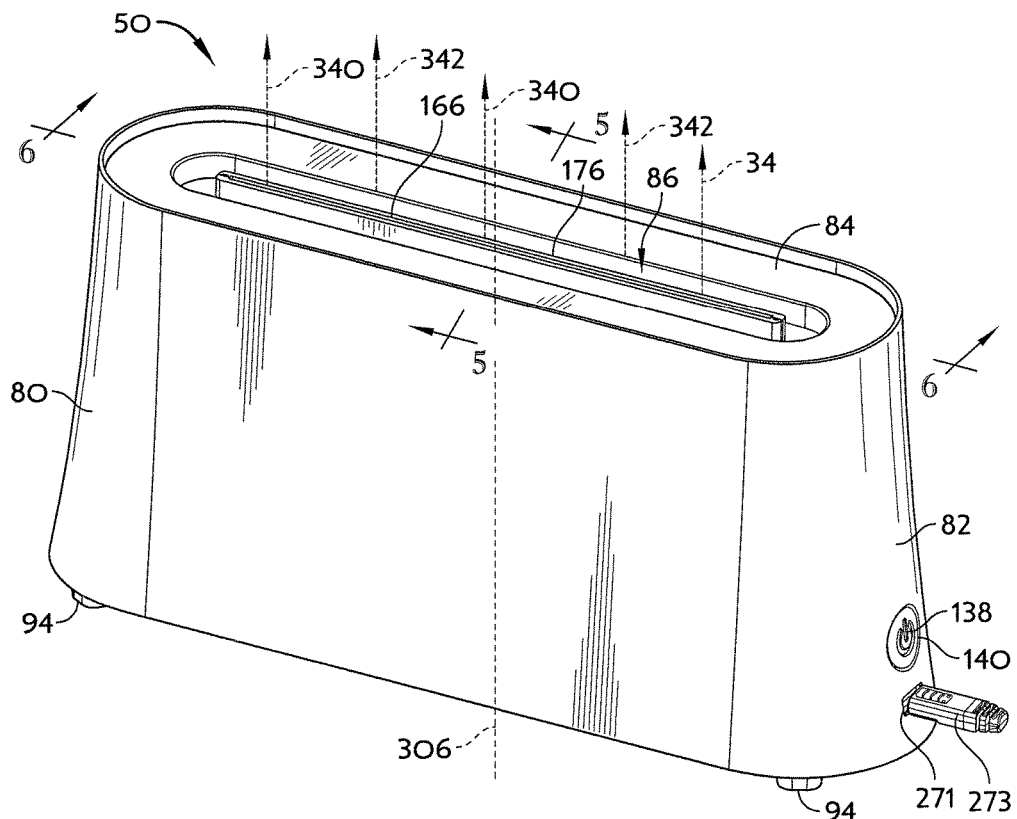
FIG. 1 perspective view of a top, front, and first side of a volatile material dispenser.
Figure 2:
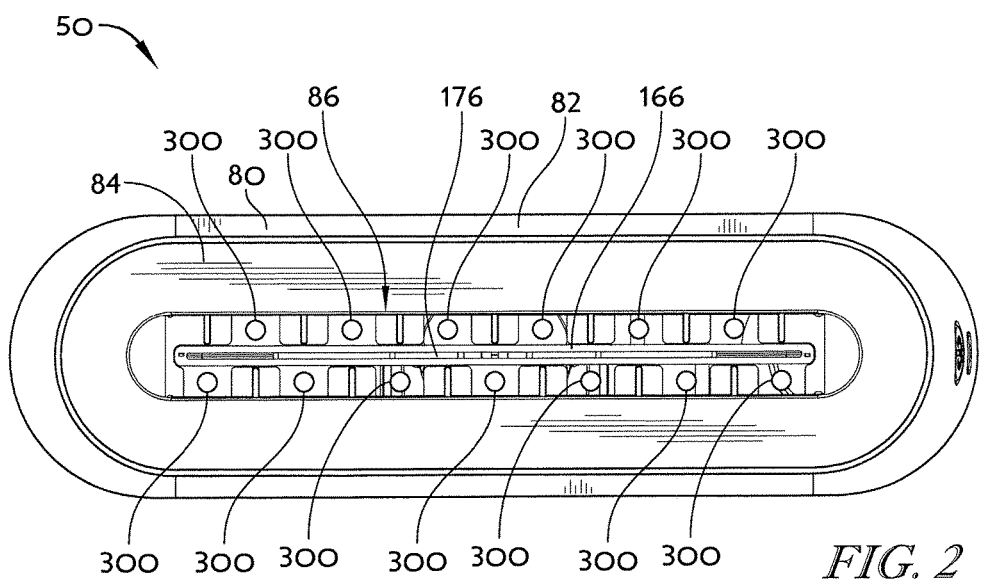
FIG. 2 is a top elevational view of the volatile material dispenser of FIG. 1, depicting an opening in a top wall of the dispenser.

Referring to the drawings, FIG. 1 depicts a volatile material dispenser 50. The dispenser 50 may be adapted to accommodate a refill 52 and dispense a volatile material from the refill. The refill 52 generally includes a container 54 for holding the volatile material therein, wherein the container 54 is adapted to be retained within the dispenser 50. The container 54 includes a body 58 for holding the volatile material and a neck 60 extending outwardly from the body 58 and providing an opening into the container 54. A retaining mechanism 62 is disposed within the neck 60 for holding a wick 64 with a first end of the wick 64 in contact with the volatile material and a second end of the wick 64 extending out of the container 54 through the neck 60. The body 58 includes a generally flat base portion 65 and four sidewalls 66 extending upwardly from the base portion 65, and a top wall 68 that joins the sidewalls 66 to the neck 60.

Although a refill 52 is shown and described with particularity, it is contemplated that any type of refill may be used with variations of the devices described herein. For example, a refill with a flexible container may be utilized. Still further, the delivery system (i.e., the wick) may be different and/or the size and/or the shape of the container may be different.

The volatile material disposed in the container 54 may include one or more active ingredients. Exemplary active ingredients include, but are not limited to, a cleaner, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Additives may additionally be included in the volatile material, such as, for example, fragrances and/or preservatives.

The volatile material within the container 54 preferably includes less than about 1.0% by weight active ingredient, with the rest of the volatile material being composed of water and other components that keep the active ingredient suspended within the water. The volatile material more preferably includes less than about 0.50% active ingredient. In illustrative embodiments, the active ingredient comprises one or more fragrance components.

Referring to FIG. 1, the dispenser 50 includes a housing 80 that includes a continuous sidewall 82 that is generally oblong in shape (i.e., straight edges and circular ends) and a top wall 84 having an opening 86 therethrough, wherein the opening 86 is generally oblong in shape. While the sidewall 82 of the housing 80 and the opening 86 are generally oblong in shape, the sidewall 82 and/or the opening 86 may have any other suitable shape and need not have the same shape. For example, one or both of the sidewall 82 and the opening 86 may be square-shaped, rectangular, elliptical, circular, oval-shaped, pentagonal, hexagonal, or any other suitable geometric shape.

Figure 5:
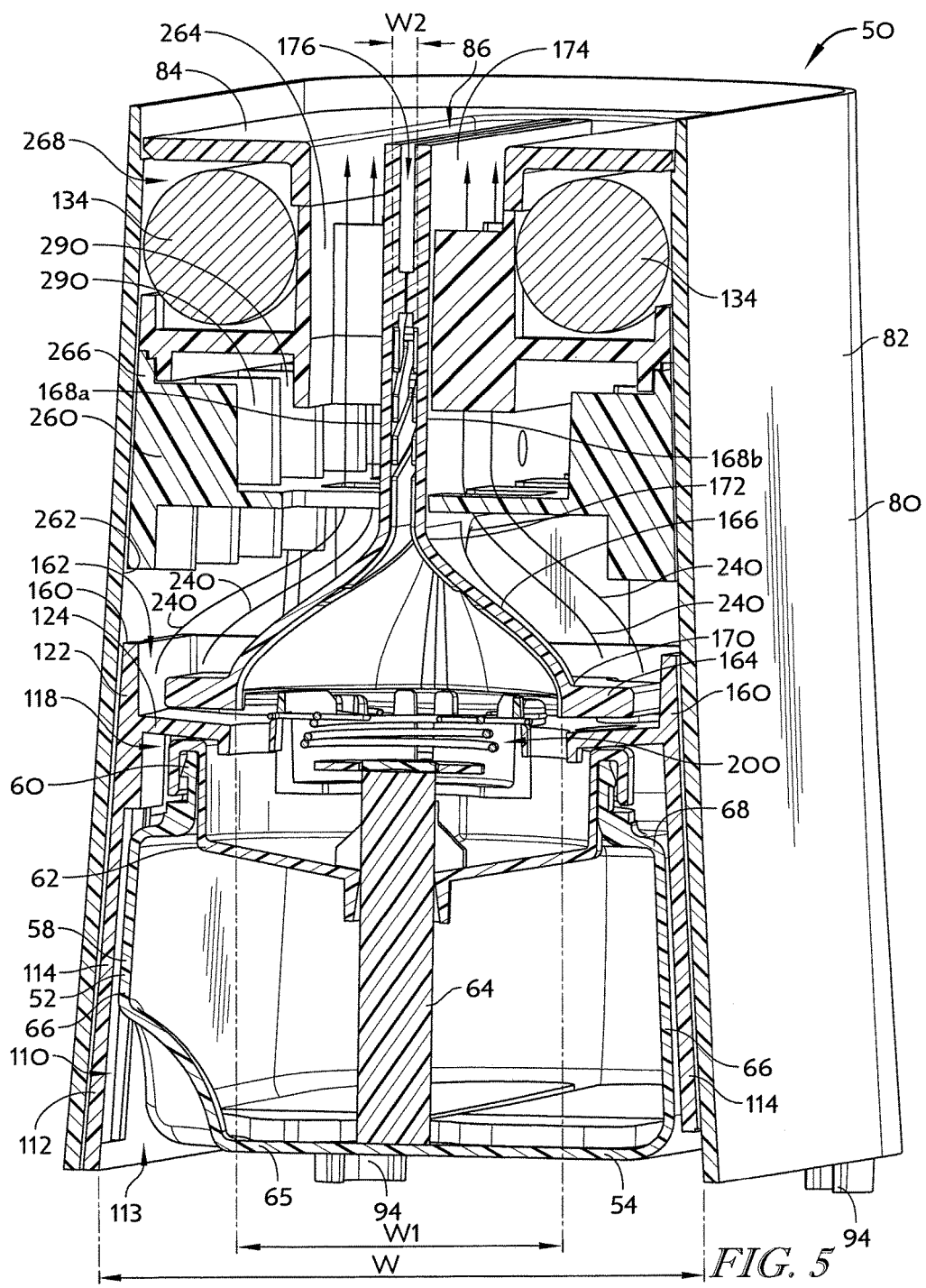
FIG. 5 is a rotated cross-sectional view taken generally along the lines 5-5 of FIG. 1, depicting a wick extending from a refill, wherein the wick is in fluid communication with a piezoelectric actuator that dispenses volatile material from the wick into the manifold, wherein air flowing around the manifold moves the volatile material away from the dispenser and, when used in combination with light sources, simulates a moving flame.
Figure 6:
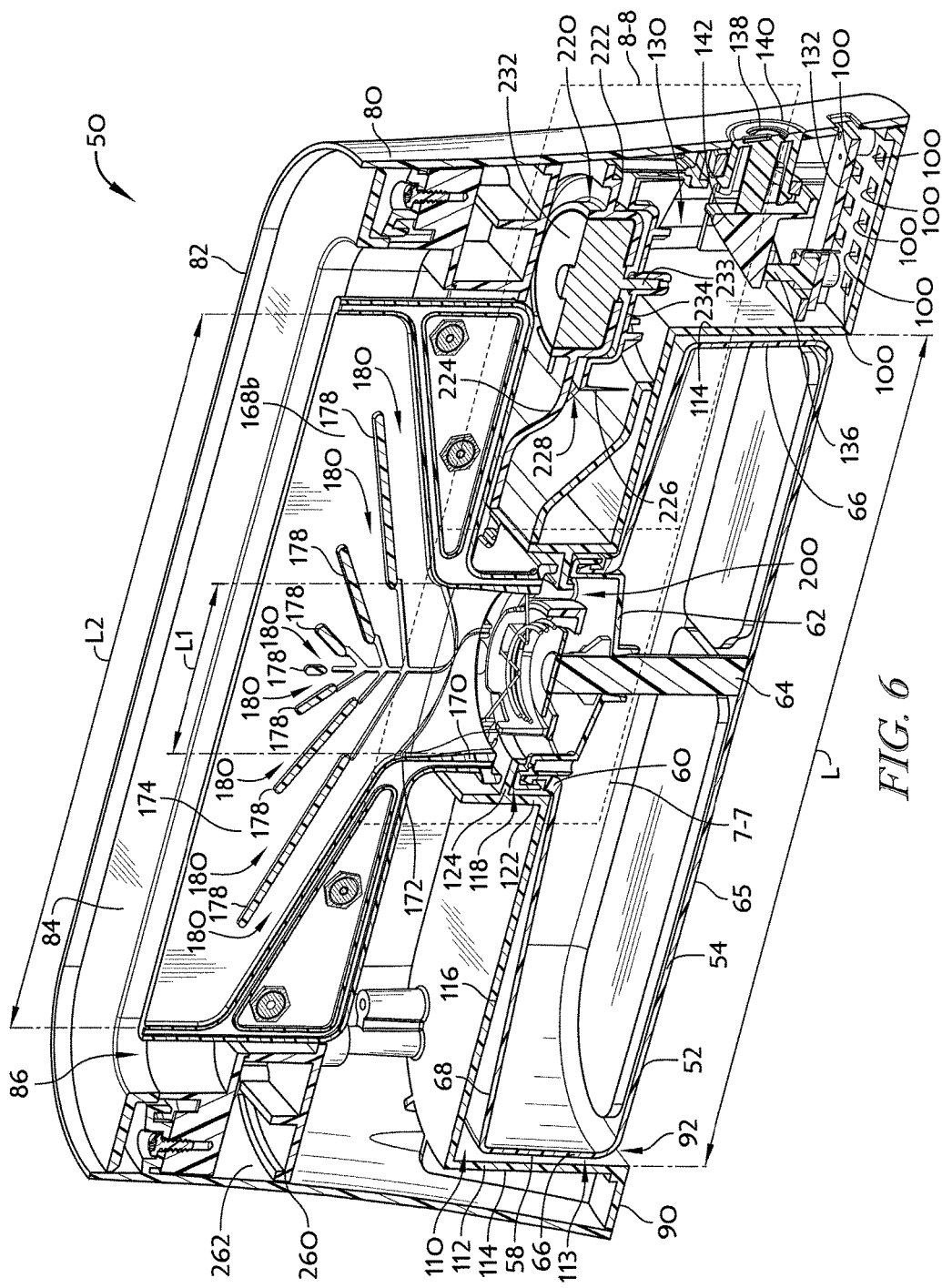
FIG. 6 is a rotated cross-sectional view taken generally along the lines 6-6 of FIG. 1, depicting the refill, the piezoelectric actuator, and the manifold of FIG. 5 and further depicting an air flow generator that provides a flow of air around the manifold.
Figure 7:
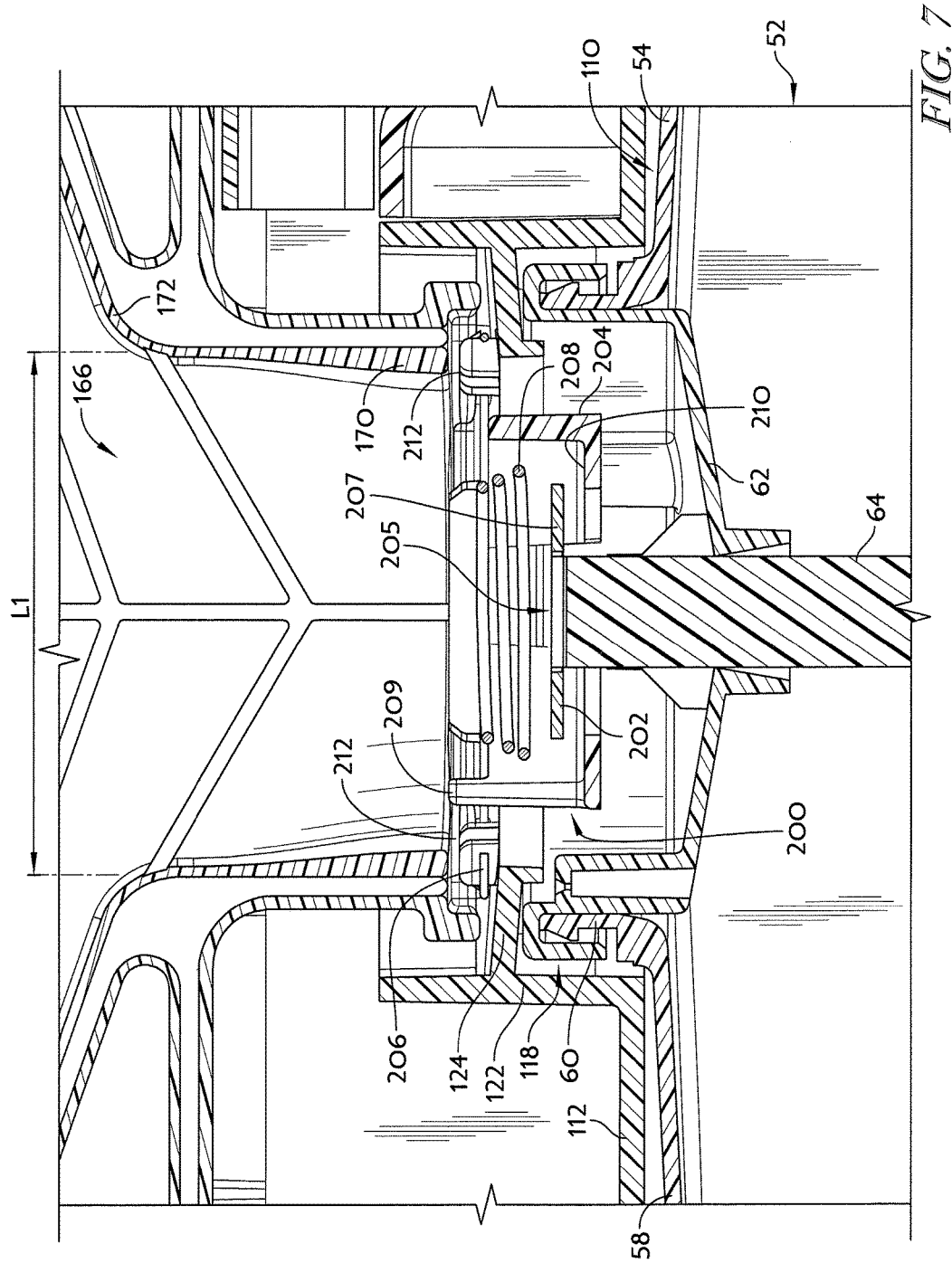
FIG. 7 is an enlarged cross-sectional view indicated by the label 7-7 in FIG. 6, depicting the wick of the refill in communication with the piezoelectric actuator of FIG. 5 and the piezoelectric actuator in fluid communication with the manifold.
Figure 8:
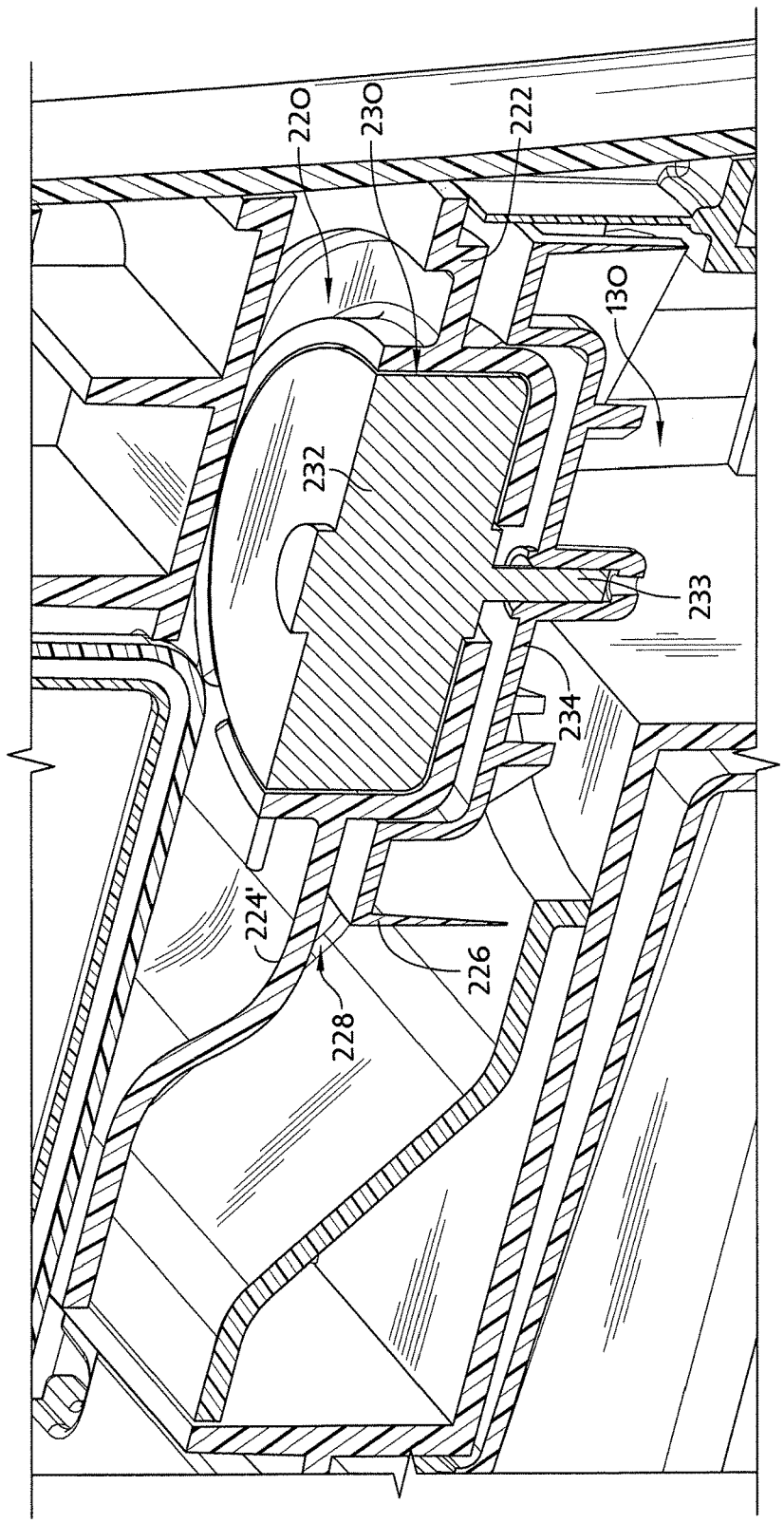
FIG. 8 is an enlarged, rotated cross-sectional view indicated by the label 8-8 in FIG. 6 and depicting the air flow generator.

The dispenser 50 also includes a partial bottom wall 90, as best seen in FIG. 6, having an opening 92 disposed therethrough for insertion of the refill 52. Optionally, a hinged door, cover, or other selectively openable cover may be connected to the bottom wall 90. Optionally, the housing 80 and the refill 52 may be configured for the refill 52 to sit on the surface and/or the refill 52 may be inserted through the sidewall 82. As seen in FIGS. 1 and 3-5, a plurality of feet 94 may extend from the bottom wall 90 to support the dispenser 50 on a surface (not shown) and/or to space the bottom wall 90 of the dispenser 50 from the surface. Any number of feet 94 is possible. Referring to FIGS. 4 and 6, one or more air flow openings 100 may be disposed within the bottom wall 90, for example, to aid in air flow through the dispenser 50, as will be discussed in greater detail below.

As best seen in FIGS. 5 and 6, a cavity 110 is formed in a lower section of the dispenser 50, wherein the cavity 110 is in communication with the opening 92 in the bottom wall 90 for holding the refill 52. The cavity 110 is formed by a refill housing 112 that includes a first section 113 that extends generally along a length L and a width W of the dispenser 50, as seen in FIGS. 5 and 6. The first section 113 is formed by vertical sidewalls 114 and a top wall 116 that form the refill housing 112. The cavity 110 further includes a second section 118 that extends upwardly from a center of the first section 113 and which is formed by a cylindrical wall 122 extending upwardly from the top wall 116 and an annular wall 124 extending inwardly from the cylindrical wall 122. The refill 52 is inserted through the opening 92 into the cavity 110 such that the neck 60 and the wick 64 of the refill 52 are disposed within the second section 118 of the cavity 110 and the container 54 of the refill 52 is disposed within the first section 113 of the cavity 110. After the refill 52 is inserted into the cavity 110, the hinged door or other cover, if present, is closed to retain the refill 52 within the cavity 110.

Figure 3:
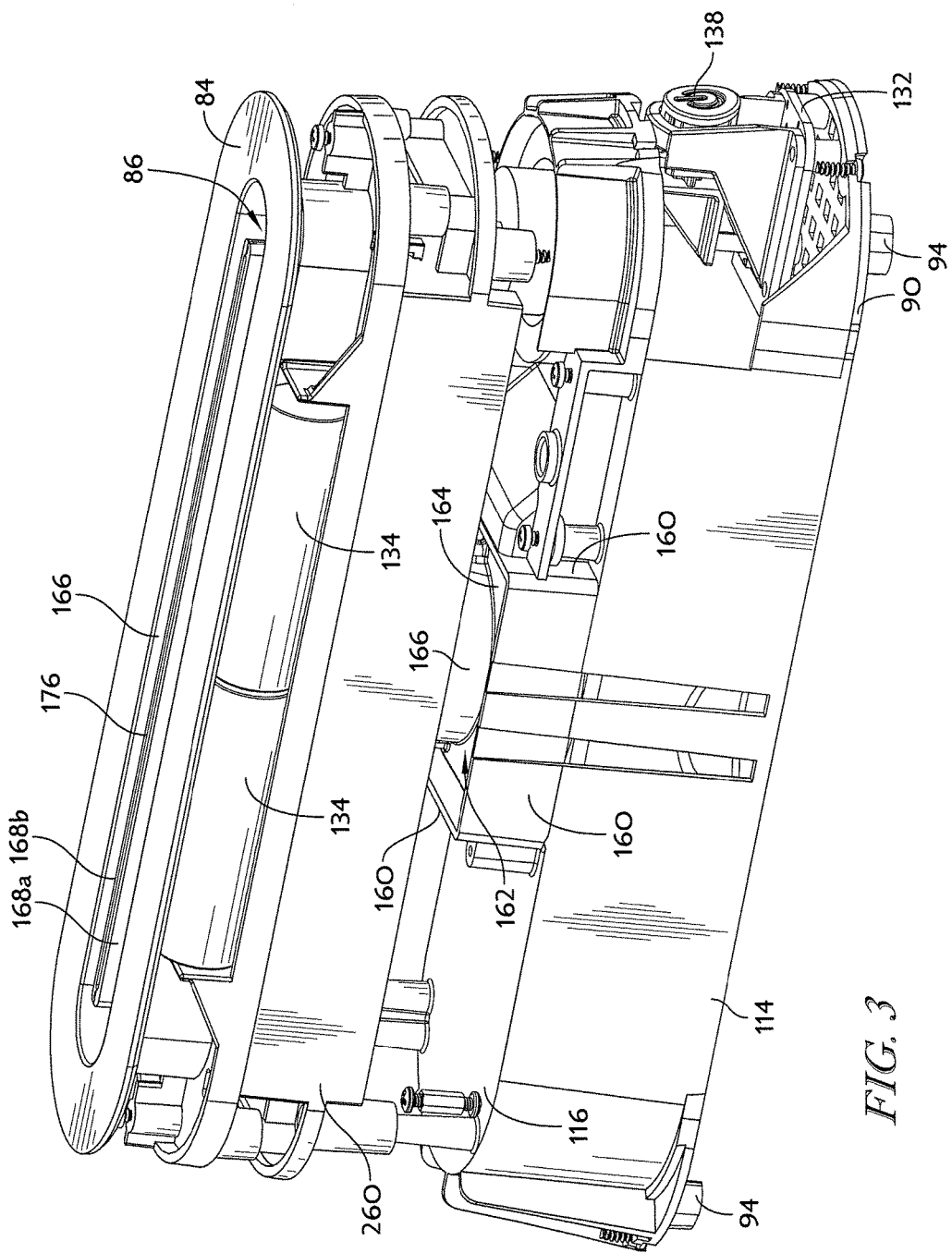
FIG. 3 is a view similar to the view of FIG. 1 with a sidewalls and a top wall removed from the dispenser to depict internal components of the dispenser.
Figure 4:
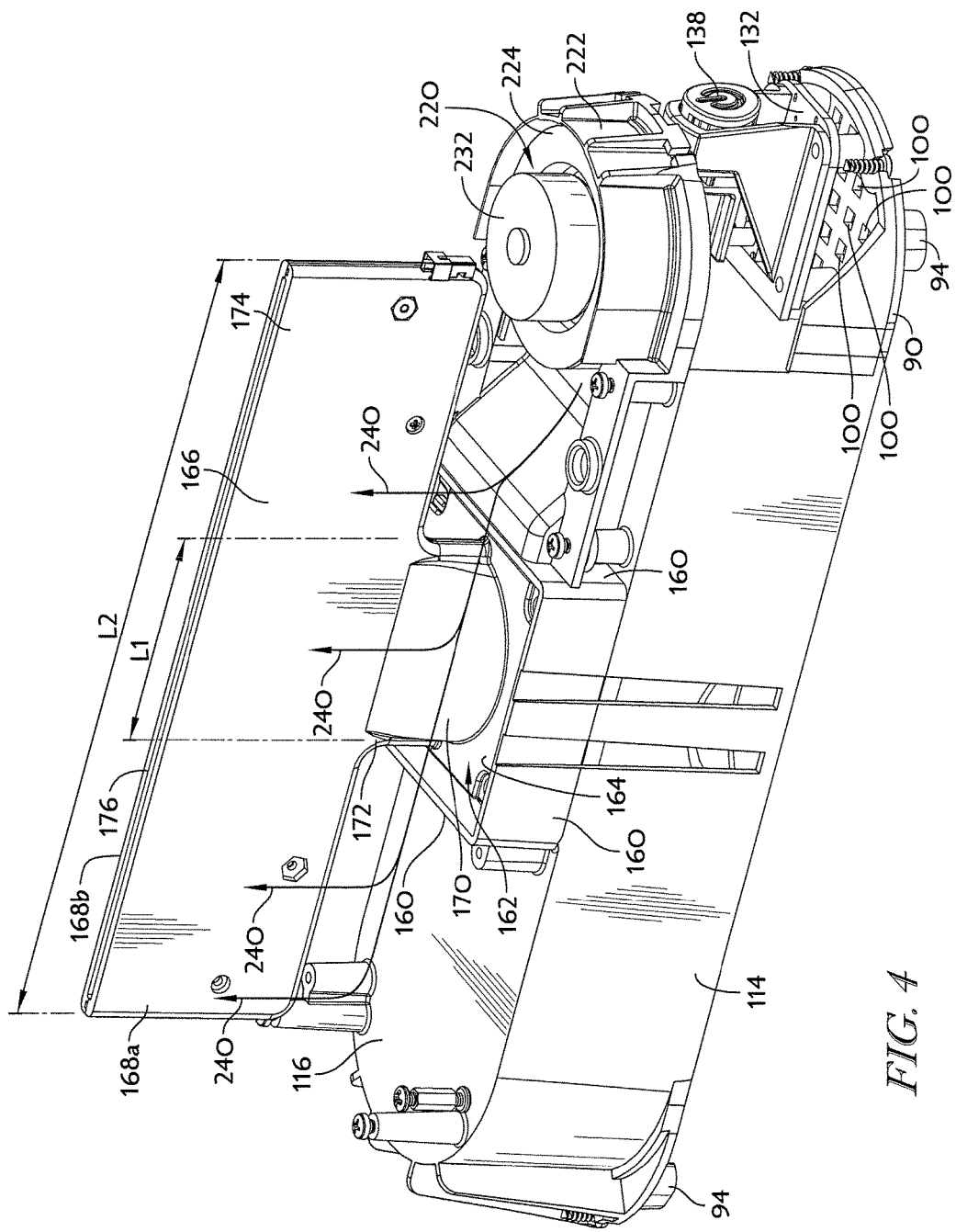
FIG. 4 is a view similar to the view of FIG. 3 with further components removed from the dispenser of FIG. 1 to illustrate a manifold through which volatile material is released and around which a flow of air is released.

Referring to FIGS. 3, 4, and 6, a compartment 130 is formed between a vertical sidewall 114 forming the cavity 110 and the housing 80. A circuit board 132, for example, an application specific integrated circuit, a microcontroller, or any other controller, is housed within the compartment 130. The circuit board 132 is electrically connected to batteries 134, the location of which will be discussed in greater detail hereinbelow. A switch 136 extends from the circuit board 132, wherein activation of the switch 136 turns the dispenser 50 on and off. In particular, a button 138 extends through a hole 140 within the housing 80 such that the button 138 is accessible to a user of the dispenser 50. An actuator arm 142 extends from a rear side of the button 138 and is positioned above the switch 136. When a user presses a front side of the button 138, the actuator arm 142 depresses the switch 136 to turn the device on or off. Optionally, the switch 136 may operate to alter any function of the dispenser 50, for example, a fan speed, a volatile material emission rate, a light intensity, or another other suitable function. Still further, the dispenser 50 may include any number of switches that operate any number of different functions of the dispenser 50. In an illustrative embodiment, the dispenser 50 includes an automatic shut-off function that deactivates the dispenser 50 after a particular period of time, for example, 3 hours.

A plurality of walls 160 extend upwardly from the top wall 116 of the refill housing 112, as seen in FIGS. 3-5, wherein the walls 160 form a generally square-shaped cavity 162. A base 164 of a manifold 166 is disposed within the square-shaped cavity 162 to provide stability and alignment to the base 164. The base 164 may also secured to the top wall 116 using a plurality of fasteners. As seen in FIG. 5, the manifold 166 includes opposing manifold walls 168a, 168b that curve inwardly from a first end 170 of the manifold 166 adjacent the base 164, wherein the manifold 166 has a width W1 and a length L1, to a central portion 172 of the manifold 166, wherein the manifold has a width W2 and the length L1. At the central portion 172 of the manifold 166, a length of the manifold 166 increases to L2, which is much greater than the length L1. The length L2 is generally constant between the central portion 172 and a second end 174 of the manifold 166. As best seen in FIGS. 1-4, the manifold 166 terminates in an exit channel 176 that is generally linear in shape. While a linear exit channel 176 is depicted, the exit channel 176 need not be linear, for example, the exit channel 176 may be curved, wavy, circular, square-shaped, or may have any other shape, pattern, or form. Referring to FIG. 6, the manifold 166 further includes a plurality of ribs 178 that form guidance channels 180 within the manifold 166. Specifically, the channels 180 are formed between the ribs 178 to guide a mist through the manifold 166, as will be discussed in greater detail hereinafter, and to evenly distribute the mist across the length L2 of the manifold 166.

In an illustrative embodiment, the shape of the manifold 166 may change. For example, the manifold 166 may be constructed of a flexible material and may be molded into different shapes by a user or a mechanical system may change the shape of the manifold 166, for example, based on a selection by a user and/or based on a pre-programmed pattern.

As best seen in FIG. 7, a piezoelectric assembly 200 is positioned adjacent the annular wall 124 disposed between the cavity 110 and the manifold 166. The piezoelectric assembly 200 includes a piezoelectric actuator 202, an actuator bracket 204, a wireform 206, and a spring 208. More specifically, the actuator 202 is held against an annular lower lip 210 of the bracket 204, the spring 208 is positioned against an outer edge of the actuator 202, and the wireform 206 is disposed through a top of the bracket 209 to compress the spring 208 to retain the actuator 202 in position. Ends of the wireform 206 are positioned around posts 212 extending from the annular wall 124 to retain the piezoelectric assembly 200 in position.

The piezoelectric actuator 202 includes a center hole 205 and an orifice plate 207 that extends across the hole 205 on an underside of the actuator 202. In an illustrative embodiment, the orifice plate 207 includes a plurality of orifices having a diameter of between about 5 microns and about 7 microns. The piezoelectric actuator 202 may be made from any material having piezoelectric properties and which causes the material to change dimensionally in a direction perpendicular to a direction of an applied electric field. Illustrative examples of suitable materials include, but are not limited to, lead zirconate titanate (PZT) or lead metaniobate (PN).

While a particular piezoelectric actuator 202 is described, any actuator 202 may be utilized, for example, a piezoelectric vibrating mesh actuator, a piezoelectric standing wave actuator, a piezoelectric vibrating needle, or any other suitable piezoelectric actuator. Further, while a piezoelectric actuator is depicted, any type of actuator capable of emitting volatile material in the form of a mist may be utilized, for example, a heater, a venturi, or any other suitable actuator.

Referring to FIG. 6, when the refill 52 is inserted into the cavity 110, the wick 64 thereof contacts the orifice plate 207. When an electric field is applied to the piezoelectric actuator 202, the piezoelectric actuator 202 expands and contracts in a radial direction, thereby causing the orifice plate 207 to vibrate in an axial direction, forcing volatile material retained within the pores of the orifice plate 207 away from the piezoelectric actuator 202 and into the manifold 166. The dispenser 50 may be configured to continuously actuate the piezoelectric actuator 202. In this manner, a continuous mist of volatile material is emitted from the dispenser 50. Alternatively, the piezoelectric actuator 202 may be deactivated for short periods of time and/or the flow rate from the piezoelectric actuator 202 may change to create different mist patterns (and/or different lighting patterns, as discussed in detail below).

Referring to FIGS. 4, 6, and 8, an air flow generator 220, for example, a blower, a fan, and/or any other suitable device(s) for creating a flow of air, is disposed above the compartment 130. Air is forced from the air flow generator 220 at a rate of between about 0.2 cubic feet per minute (CFM) and about 1.0 CFM. In an illustrative embodiment, air is forced from the air flow generator at a rate of about 0.4 CFM. The air flow from the air flow generator 220 may be a function of a length L2 of the manifold. More specifically, as the length L2 increase, the air flow rate will increase. An air flow rate factor is defined as the air flow rate (CFM) per length (inch). In an illustrative embodiment, the air flow rate factor is between about 0.04 CFM/inch and about 0.16 CFM/inch. In a further illustrative embodiment, the air flow rate factor is between about 0.06 CFM/inch and about 0.10 CFM/inch. In yet another illustrative embodiment, the air flow rate factor is about 0.08 CFM/inch. The flow of air may be static in that the rate of air flow does not change or the flow of air may be dynamic. In an illustrative example, the flow of air may change for intervals of, for example, 1 second, 2 seconds, 5 seconds, or any other time interval to create an effect. In yet another illustrative embodiment, the rate of air flow from the air flow generator 220 may be changed continuously to create different effects. Any number of dynamic air flow patterns may be created. Still further, a user may be allowed to select from a number of different air flow patterns including a static pattern and/or one or more dynamic patterns.

In a further embodiment, the air flow generator 220 may be turned off such that the air flow rate is 0 CFM. In such an embodiment, the mist emitted from the piezoelectric actuator 202 is forced out of the manifold 166 and is not entrained within a flow of air.

The air flow generator 220 is held in place by a fan bracket 222 having an upper bracket 224 and a lower bracket 226. As seen in FIG. 4, the lower bracket 226 is affixed to the top wall 116 of the refill housing 112 by any suitable means, for example, fasteners. The lower bracket 226 further includes an opening 228 therethrough. The upper bracket 224 is connected to the lower bracket 226 by any suitable means and includes a cavity 230 into which a motor 232 of the air flow generator 220 is press fit. The motor 232 includes a shaft 233 extending downwardly therefrom, wherein an impeller 234 is press fit onto an end of the shaft 233 to rotate the impeller 234 upon activation of the motor 232. The impeller 234 is aligned with the opening 228 to draw air through the openings 100 in the bottom wall 90 of the housing 80, wherein the air flow generator 220 creates a positive pressure that pushes air upwardly through the housing 80 along air flow paths 240 (only some of which are labeled), as seen in FIGS. 4 and 5. The air flow paths 240 and the flow of air through the dispenser 50 will be discussed in greater detail hereinafter.

As best seen in FIGS. 3, 5, and 6, a support structure 260 is connected by fasteners or other suitable means to the top wall 116 forming the cavity 110, to an inner surface 262 of the housing 80, and/or to the upper bracket 224 of the fan bracket 222. The support structure 260 may be generally oblong in shape and includes inner and outer walls 264, 266 spaced from one another and forming a compartment 268 therebetween. As seen in FIG. 3, the batteries 134 may be disposed in the compartment 268 and electrically connected to the circuit board 132 for powering the dispenser 50. Optionally, the dispenser 50 may include a cord extending from the housing 80, for example adjacent the circuit board 132, for plugging into a conventional electrical outlet. Still optionally, the dispenser 50 may include a universal serial bus (USB) port 271 for connecting a USB plug 273 (as seen in FIG. 1) that can power the dispenser 50 and/or transfer information, such as volatile material emission programs, lighting programs, and/or air flow programs, to the dispenser 50. For example, a USB power cable may be coupled between the USB plug 273 of the dispenser 50 and a personal computer, such as, for example, a computer, a tablet, a mobile phone, and the like. The USB power cable may allow serial communications between the dispenser 50 and the personal computer such that a user of the personal computer may control the dispenser 50, for example, the air flow rate of the air flow generator 220, the output rate of the piezoelectric actuator 202, and/or the intensity of LEDs 300. Still further, the USB power cable may allow a user of the personal computer to selected a program, as discussed above, and/or create their own program. The dispenser 50 may include one or more of the disclosed power supplies.

Figure 9:
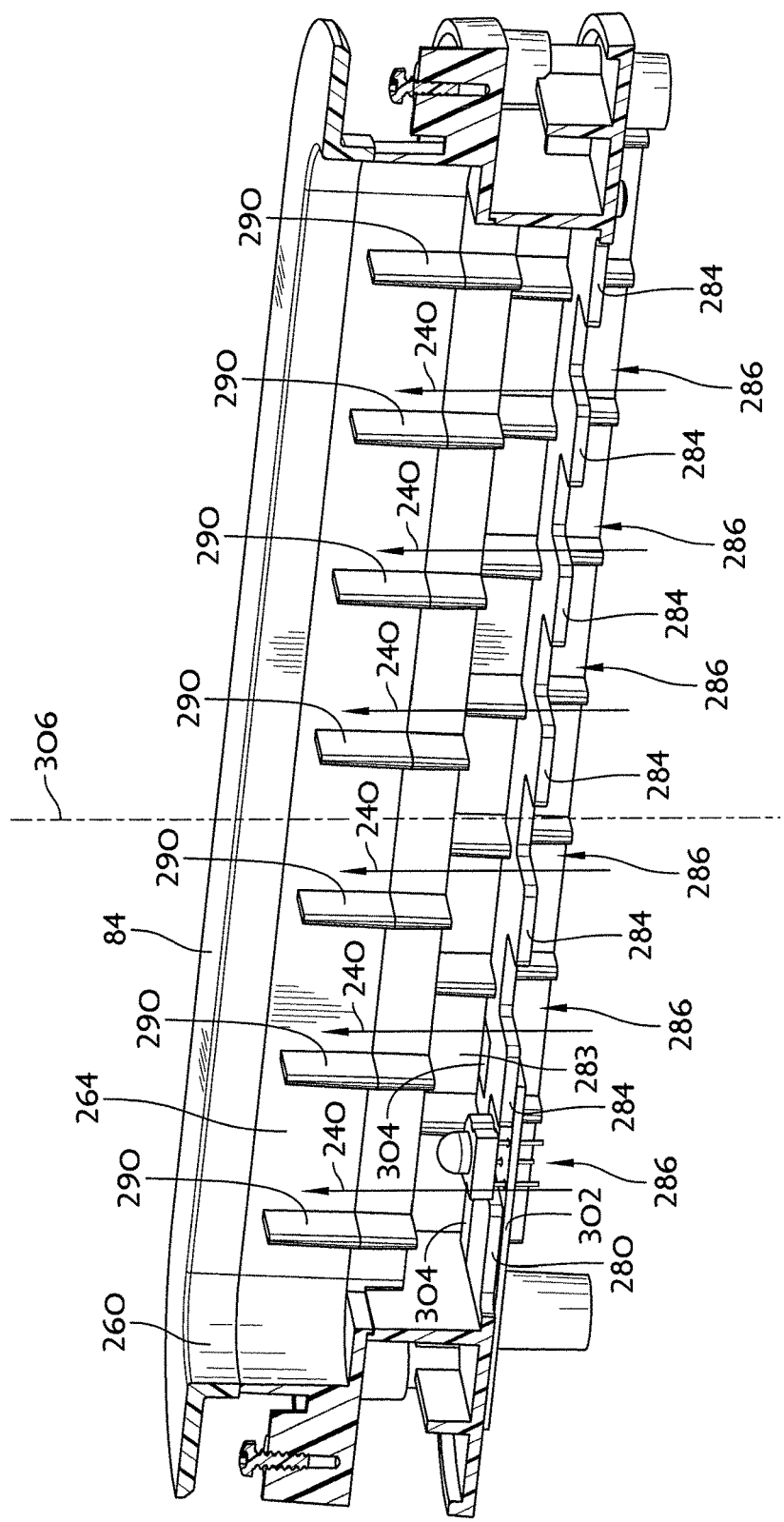
FIG. 9 is a rotated cross-sectional view taken generally along the lines 6-6 with the manifold and housing removed therefrom to shown baffles formed around the manifold for directing air through various air flow pathways, wherein an opposite side of the dispenser includes similar baffles.

The inner wall 264 of the support structure 260, as seen in FIG. 9, extends to the top wall 84 of the housing 80 and functions to guide the flow of air from the air flow generator 220 around the manifold 166. Specifically, the inner wall 264 includes a first set of baffles 280 extending inwardly from a peripheral surface 283 thereof. The baffles 280 are shown as having alternating air blocking members 284 and gaps 286 that are generally rectangular or square-shaped, but the baffles 280 may take any other suitable form.

A second set of baffles in the form of vertical plates 290 extends inwardly from the peripheral surface 283 of the inner wall 264 of the support structure 260 above the first set of baffles 280. The air blocking members 284 of the baffles 280 and the vertical plates 290 may extend from the support structure 260 to the manifold 166 to force air through air flow paths 240 created thereby. Specifically, air is forced to move through the gaps 286 formed by the first set of baffles 280 and between adjacent vertical plates 290. In this manner, the flow of air is distributed evenly through each of the air flow paths 240 around the manifold 166 such that the flow of air exits the opening 86 evenly around the entire manifold 166.

While the flow of air from the air flow generator 220 is disclosed herein as taking an air flow path around the manifold 166, the air flow path may alternatively or additional move through the manifold 166 and carry the volatile material out of the manifold 166. In an illustrative embodiment, the flow of air moves around the manifold and through the manifold.

The top wall 84 of the housing 80 may be selectively attached to the support structure 260 or the sidewall 82 of the housing 80. In particular, it may be preferable that the batteries 134 be accessible to a user for ease in replacement thereof. The top wall 84 may therefore be attached to the support structure 260 and/or the sidewall 82 of the housing 80 by a snap fit, a friction fit, or any other suitable method by which the top wall 84 may be easily removed.

One or more light sources 300 may be located within the housing 80. The light sources 300 may comprise any suitable light sources, for example, one or more light emitting diodes (LED), halogen bulbs, and/or incandescent bulbs, and the light sources 300 may emit any color of light. For example, in an illustrative embodiment, one or more of the LEDs 300 may be yellow or amber in color to create the illusion of a flame. In another illustrative embodiment, one or more of the LEDs 300 may be blue in color to create the illusion of a waterfall. Optionally, any other natural phenomena may be emulated with any number of different LEDs 300. Optionally, one or more of the LEDs 300 could be blue, white, red, green, or any other suitable color. Further, the LEDs 300 need not be the same color and/or one or more of the LEDs 300 may be a multi-color LED and the color thereof may change. While thirteen LEDs 300 are depicted, any suitable number of LEDs 300 may be utilized.

In an illustrative embodiment, as best seen in FIG. 9, thirteen LEDs 300 are positioned within the gaps 286 formed by the first set of baffles 280. In particular, as seen in FIG. 9, a single LED 300 is depicted on a board 302 that is attached to the air blocking members 284 and extends across the gaps 286. The LED 300 is connected to the board 302 and includes appropriate wiring to connect the board 302 to the circuit board 132. In the illustrated embodiment, the board 302 may impede movement of air through the gaps 286, in which case, apertures 304 may be formed in the baffles 280 to allow air to move therethrough. Each LED 300 may be disposed on a separate board or a single board 302 may extend along the baffles 280 on one side of the dispenser 50 for holding a plurality of LEDs 300. Optionally, the LEDs 300 may be positioned in any location that allows light to be projected out of the opening 84 and onto the mist of volatile material emitted from the dispenser 50.

In an illustrative embodiment, the LEDs 300 may be positioned below the top wall 84 of the housing 80 and may be longitudinally aligned within a profile of the opening 86. More specifically, the LEDs 300 may be spaced along a longitudinal axis 306 and within an area of the opening 86. In this manner, when looking directly down into the dispenser 50 (as seen in FIG. 2), the LEDs 300 may be seen within the profile of the opening 86. Alternatively, the LEDs 300 may be placed immediately below the opening 86, within the profile of the opening 86, and/or adjacent the opening 86.

The LEDs 300 may have a total luminosity output of less than about 50 lumens depending on a number of LEDs 300. In an illustrative embodiment, the total luminosity output of the LEDs 300 is about 16 lumens. In another illustrative embodiment, the total luminosity output of the LEDs 300 is about 1 lumen. The light emitted by the LEDs 300 may be static in that the luminosity of the LEDs 300 remains constant or the light emitted by the LEDs 300 may be dynamic. In an illustrative embodiment, the LEDs 300 may continuously flicker, the luminosity of the LEDs 300 may change on a periodic basis, and/or any other dynamic lighting patterns may be implemented. Still further, a number of lighting patterns may be available and selectable by a user. Still optionally, the dispenser 50 may include a switch or other mechanism to allow a user to turn the LEDs 300 on and off and/or may include a program that automatically turns the LEDs 300 on and off, for example, at particular times of the day. Additionally, the dispenser may contain a light sensor to measure the ambient light surrounding the dispenser and adjust the intensity of the LEDs accordingly.

During use of the dispenser 50, any number of the components (i.e., the air flow generator 220, the piezoelectric actuator 202, and the LEDs 300) may be activated. If the piezoelectric actuator 202 is activated, the volatile material is continuously dispensed as a mist into the manifold 166 and released through the exit channel 176 of the manifold 166. A droplet size of the volatile material after emission by the piezoelectric actuator 202 is driven by the particular volatile material formulation, but may be about 10 microns or less. If the air flow generator 220 is activated, air is forced along the flow paths 240 and through the opening 84, the volatile material mist becomes entrained in the air flow and is carried away from the dispenser 50. As seen in FIG. 1, a direction of movement 340 of the volatile material mist and the direction of air flow 342 are parallel and/or coincident. While a few flow paths for the volatile material mist and the air flow are depicted in FIG. 1, it should be understood that the volatile material mist is emitted through an entire length of the exit channel 176 and air is released around the entire opening 84, thereby surrounding the exit channel 176 and the volatile material mist with the flow of air. If the LEDs 300 are activated, the amber color (or other color) of the LEDs 300 is projected into the moving mist, which creates a real looking simulated flame.

A height of the mist emitted from the dispenser 50 is dependent on the air flow from the air flow generator 220 and the humidity conditions in the surrounding area. For example, if the humidity in the surrounding area is high, the mist lingers longer and tends to rise and, if the humidity in the surrounding area is low, the mist dissipates more quickly and does not rise as much. The dispenser 50 may be equipped with a humidity sensor that may detect the humidity in the surrounding area. Based on the readings of the humidity sensor, the dispenser 50 may automatically adjust the air flow rate of the air flow generator 220 and/or the output rate of the piezoelectric actuator 202 to optimize the user experience.

In an illustrative embodiment, the dispenser 50 is capable of providing a pleasant scent and a simulated flame without heat or actual fire. In this manner, the dispenser 50 functions at ambient temperature to create what appears to be a real flame (and not just a flickering light).

While not shown in the figures, the dispenser 50 may include a shroud that is formed as part of the sidewall 82 of the housing 80 or as a separate piece and attached to the housing 80 adjacent the top wall 84. If used, the shroud may generally surround the opening 86 to enclose the mist and the simulated flame. In this manner, the simulated flame appears to more realistic. The shroud may be of any height, size, and/or material, but is preferably clear or translucent to allow a user to view of the simulated flame.

The dispensers disclosed herein may further include one or more openings in the housing to allow for the volatile material to be dispensed from the housing to the surrounding environment. The housing may include a variety of internal implements to help secure the various refills disclosed herein, such as, for example, snaps, ridges, undercuts, lips, notches, and/or other attachment methods. The dispensers may optionally include one or more refills and may operate using a variety of timing sequences as known in the art.

Any of the embodiments described herein may be modified to include any of the structures or methodologies disclosed in connection with other embodiments.

Further, although directional terminology, such as front, back, upper, lower, vertical, horizontal, etc. may be used throughout the present specification, it should be understood that such terms are not limiting and are only utilized herein to convey the orientation of different elements with respect to one another.

All documents cited in the Detailed Description of the Invention are, in relevant part, incorporated herein by reference; the citation of any document is not to be construed as an admission that it is prior art with respect to the present invention.

INDUSTRIAL APPLICABILITY

The present invention provides volatile material dispensers and methods of dispensing volatile materials in the form of a mist. In combination with an air flow generator and/or light sources, a life-like simulated flame or waterfall may be created to provide a relaxing ambiance.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A portable volatile material dispenser comprising:
   a housing;
   an opening formed within a wall of the housing;
   a volatile material actuator selected from the group consisting of a vibrating mesh piezoelectric actuator, a vibrating needle piezoelectric actuator, an aerosol, and a standing wave piezoelectric actuator, wherein the volatile material actuator is spaced from the opening and in fluid communication with a manifold having an interior and an exterior, the manifold dispensing a volatile material in the form of a mist through the interior of the manifold, to an exit channel of the manifold, and out of the opening;
   a container holding a fluid containing the volatile material, wherein the container is disposed within the housing and in communication with the volatile material actuator, the container receiving a wick to transport the fluid to the volatile material actuator;
   an air flow generator within the housing and creating a flow of air along the exterior of and concentric with the manifold, past the exit channel of the manifold, and out of the dispenser through the opening, to combine with and move the mist away from the dispenser; and
   a plurality of light emitting diodes disposed within the housing longitudinally below and aligned with a profile of the opening and surrounding the manifold for illuminating the mist emitted from the dispenser to simulate a flame.

2. The portable dispenser of claim 1, wherein the manifold is also in fluid communication with the air flow generator to direct the mist from the volatile material actuator, wherein the air from the air flow generator is also directed through the interior of the manifold.

3. The portable dispenser of claim 2, wherein the manifold has a shape that is selected from the group consisting of: linear, circular, square-shaped, and a wave.

4. The portable dispenser of claim 1, wherein emission of volatile material from the actuator is interrupted to change an effect of the simulated flame.

5. The portable dispenser of claim 1, further including a humidity sensor for detecting a humidity of an area surrounding the dispenser.

6. The portable dispenser of claim 1, further including a universal serial bus port for connecting a universal serial bus plug between the dispenser and a personal computer.

7. The portable dispenser of claim 1, further including a light sensor for detecting ambient light surrounding the dispenser.

8. The portable dispenser of claim 1, wherein light emitted by the plurality of light emitting diodes projects out of the opening between the manifold and an edge of the wall.

9. A portable volatile material dispenser comprising:
   a housing defining a longitudinal axis extending along a height of the housing;
   an opening formed within a wall of the housing;
   a volatile material actuator selected from the group consisting of a vibrating mesh piezoelectric actuator, a vibrating needle piezoelectric actuator, an aerosol, and a standing wave piezoelectric actuator, wherein the volatile material actuator is positioned about the longitudinal axis and spaced from the opening to dispense a mist through the opening;

a container holding a fluid containing a volatile material, wherein the container is disposed within the housing and in communication with the volatile material actuator to transport the fluid to the volatile material actuator;

an air flow generator within the housing and offset from the longitudinal axis, the air flow generator having a rotational axis parallel to the longitudinal axis to create a flow of air out of the dispenser through the opening to combine with and move the volatile material in the form of the mist from the dispenser;

a manifold disposed within the housing and including an interior, an exterior, a first end proximate the volatile material actuator, and a second end that includes an exit channel disposed within and surrounded by the opening, wherein the first end is positioned to receive the mist from the volatile material actuator for transport of the mist within the interior of the manifold from the first end to the second end, wherein an edge of the wall of the housing and the second end of the manifold define a gap surrounding the second end of the manifold, and wherein the flow of air passes along the exterior of the exit channel and concentric with respect to the manifold, to move through the gap and combine with the mist to move the mist from the dispenser; and a plurality of light emitting diodes disposed within the housing in the gap such that the light emitting diodes surround the manifold and illuminate the mist emitted from the dispenser to simulate a flame.

10. The portable dispenser of claim 9, wherein the first end of the manifold forms an airflow entrance having a first length and a first width and a second end of the manifold forms an airflow exit having a second length and a second width, wherein the second length is greater than the first length and the second width is less than the first width.

11. The portable dispenser of claim 9, wherein the mist is emitted out of the second end of the manifold positioned in the opening and the flow of air is emitted from the gap surrounding the second end of the manifold.

* * * * *